(12) United States Patent
Kawabata et al.

(10) Patent No.: US 7,994,349 B2
(45) Date of Patent: Aug. 9, 2011

(54) PROCESS FOR PRODUCING OF EPOXY COMPOUND

(75) Inventors: Tomonori Kawabata, Toyonaka (JP); Hiroaki Abekawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/087,461

(22) PCT Filed: Jan. 9, 2007

(86) PCT No.: PCT/JP2007/050373
§ 371 (c)(1),
(2), (4) Date: Oct. 8, 2008

(87) PCT Pub. No.: WO2007/080995
PCT Pub. Date: Jul. 19, 2007

(65) Prior Publication Data
US 2009/0054670 A1 Feb. 26, 2009

(30) Foreign Application Priority Data

Jan. 11, 2006 (JP) .................................. 2006-003460
Sep. 27, 2006 (JP) .................................. 2006-262133

(51) Int. Cl.
*C07D 301/12* (2006.01)
*C07D 301/06* (2006.01)
(52) U.S. Cl. ........................................ 549/533; 549/531
(58) Field of Classification Search .................. 549/533, 549/531
See application file for complete search history.

(56) References Cited

U.S. PATENT DOCUMENTS
5,221,795 A  6/1993  Clerici et al.
5,972,305 A  10/1999  Park et al.

FOREIGN PATENT DOCUMENTS

| EP | 0 819 683 A | 1/1998 |
|---|---|---|
| GB | 1 209 321 A | 10/1970 |
| JP | 4-352771 A | 12/1992 |
| JP | 2002-511455 A | 4/2002 |
| JP | 2005-508362 A | 3/2005 |
| JP | 2005-514364 A | 5/2005 |
| WO | WO-99/52885 A1 | 10/1999 |
| WO | WO-03/035632 A1 | 5/2003 |
| WO | WO-03/044001 A1 | 5/2003 |

OTHER PUBLICATIONS

New Energy and Industrial Technology Development Organization Consignee Japan Chemical Innovation Institute et al. "Year 2001: The Next Generation Chemical Process Technology Development and Non-Halogen Chemistry Process Technology Development Result Reports", Mar. 2002, pp. 168-209. (with English translation).
New Energy and Industrial Technology Development Organization Consignee Japan Chemical Innovation Institute et al. "Year 2002: The Next Generation Chemical Process Technology Development and Non-Halogen Chemistry Process Technology Development Result Reports", Mar. 2003, pp. 152-180. (with English translation).
Meiers R et al., Journal of Catalysis, Academic Press, vol. 176, No. 2, Jun. 10, 1998, pp. 376-386.
"Achievement Report for the Year 2001 of Next-generation Chemical Process Technical Development and Non-halogen Chemical Process Technical Development", pp. 249-258, 2002. (With English Language Translation).
Office Action mailed Jun. 30, 2010 in European Application No. 07706715.

*Primary Examiner* — Taylor Victor Oh
(74) *Attorney, Agent, or Firm* — Birch, Stewart, Kolasch & Birch, LLP

(57) ABSTRACT

An object of the present invention is to provide an efficient process for producing an epoxy compound from olefin, oxygen and hydrogen. The process of the present invention is characterized in that an olefin, oxygen and hydrogen are reacted in a liquid phase in the presence of a titanosilicate selected from the group consisting of a crystalline titanosilicate having MEL structure, MTW structure, BEA structure, MWW structure or DON structure, a mesoporous titanosilicate and a lamellar titanosilicate, a noble metal catalyst, and a quinoid compound or a dihydro-form of quinoid compound.

17 Claims, No Drawings

PROCESS FOR PRODUCING OF EPOXY COMPOUND

TECHNICAL FIELD

The present invention relates to a process for producing an epoxy compound from an olefin, oxygen and hydrogen.

BACKGROUND ART

As a process for producing epoxy compounds from olefins, oxygen and hydrogen, for example, a process using a noble metal compound and titanosilicate is known. As a process for producing propylene oxide using a catalyst containing TS-1 and Pd, there are reported a process for producing propylene oxide which comprises reacting hydrogen/oxygen/propylene in the presence of a catalyst of Pd and Au supported on TS-1, wherein water is used as a solvent and hydroquinone is added thereto (see Heisei 12 nendo Jisedai Kagaku Process Gijutu Kaihatu Non-halogen Kagaku Process Gijutu Kaihatu Seika Houkokusho (Report of R&D projects for Technology of Next-generation Chemical Process/Technology for Non-halogen Chemical Process" FY2001 Annual Report), pp. 249-258 (2002)).

DISCLOSURE OF THE INVENTION

One object of the present invention is to provide a process for producing an epoxy compound from an olefin, oxygen and hydrogen efficiently.

Namely, the present invention relates to a process for producing an epoxy compound which comprises reacting an olefin, oxygen and hydrogen in a liquid phase in the presence of a titanosilicate selected from the group consisting of a crystalline titanosilicate having MEL structure, MTW structure, BEA structure, MWW structure or DON structure, a mesoporous titanosilicate and a lamellar titanosilicate, a noble metal catalyst, and a quinoid compound or a dihydroform of quinoid compound.

BEST MODE FOR CARRYING OUT THE INVENTION

Typical examples of the noble metal catalyst used in the present invention include palladium, platinum, ruthenium, rhodium, iridium, osmium, gold, or an alloy or a mixture thereof. Preferably, the noble metal catalyst is palladium, platinum or gold. More preferred noble metal catalyst is palladium. Palladium can be used by adding thereto and mixing with a metal such as platinum, gold, rhodium, iridium or osmium. Preferred metal to be added is platinum.

Further, these noble metal catalysts may also be added as noble metal compounds such as oxides or hydroxides of noble metals. Alternatively, a noble metal compound can be filled as it is in a reactor, followed by reducing it partially or completely with hydrogen contained in starting materials of the reaction under reaction conditions.

Usually, a noble metal catalyst 1 is used by supporting it on a carrier. A noble metal catalyst can also be used by supporting it on titanosilicate. A noble metal catalyst can also be used by supporting it on a carrier other than titanosilicate such as oxides, for example, silica, alumina, titania, zirconia, niobia, etc.; hydrates, for example, niobic acid, zirconic acid, tungstic acid, titanic acid, etc.; or carbon; and a mixture thereof. When a noble metal catalyst is supported on a carrier other than titanosilicate, a carrier supporting the noble metal catalyst can be mixed with titanosilicate and the mixture can be used as a catalyst. Among the supports other than titanosilicate, a preferred carrier is carbon. As known carbon carriers, there are an active carbon, carbon black, graphite, carbon nano-tube and the like.

As a method for preparing a noble metal catalyst supported on a carrier, a colloidal solution of a noble metal obtained by dispersing particles of the noble metal with a dispersant such as citric acid, polyvinyl alcohol, polyvinyl pyrrolidone, sodium hexametaphosphate, etc. is supported on a carrier by an impregnation method or the like and calcined in an atmosphere of an inert gas. Alternatively, a noble metal catalyst supported on a carrier can also be prepared by having a noble metal compound which can be used as a noble metal source such as a nitrate salt of a noble metal, e.g., palladium nitrate, a sulfate salt of a noble metal, e.g., palladium sulfate dihydrate, a halogenide of a noble metal, e.g., palladium chloride, a carboxylate salt of a noble metal, e.g., palladium acetate or an ammine complex, e.g., Pd tetraammine chloride, supported on a carrier by an impregnation method or the like, followed by reduction with a reducing agent; or it can also be prepared by first changing to a noble metal to its hydroxide with an alkali such as sodium hydroxide, followed by reduction with a reducing agent in a liquid phase or a gas phase. Examples of the reducing agent to be used in case of the reduction in liquid phase include hydrogen, hydrazine monohydrate, formaldehyde, sodium borohydride, etc. When using hydrazine monohydrate or formaldehyde, the addition of an alkali is also known. Examples of the reducing agent to be used in case of the reduction in gas phase include hydrogen, ammonia, and the like. The catalyst can also be prepared by calcining and reducing a noble metal source supported on a carrier in the presence of hydrogen gas. A preferred reduction temperature is varied depending on a noble metal source supported, but generally from 0° C. to 500° C. Moreover, the catalyst can also be prepared by having an ammine complex of a noble metal, e.g., Pd tetraammine chloride supported on a carrier by an impregnation method or the like, followed by reduction with ammonia gas generated upon thermal decomposition in an atmosphere of an inert gas. The reduction temperature is varied depending on an ammine complex of a noble metal, but in case of using Pd tetraammine chloride, generally from 100° C. to 500° C. and preferably 200° C. to 350° C.

In any methods, if necessary, it is possible to activate the resultant catalyst by heat treatment in an atmosphere of an inert gas, ammonia gas, vacuum, hydrogen or air. Further, after filling an oxide or hydroxide compound of a noble metal into a reactor, it can be reduced under reaction conditions.

In this way, the resultant carrier supporting a noble metal catalyst generally contains a noble metal catalyst in a range of 0.01 to 20% by weight, preferably 0.1 to 5% by weight.

The weight ratio of the noble metal catalyst to titanosilicate (weight of a noble metal to weight of titanosilicate) is preferably 0.01 to 100% by weight, more preferably 0.1 to 20% by weight.

Titanosilicate is a generic name of a substance in which a part of Si in a porous silicate ($SiO_2$) is replaced with Ti. Ti of titanosilicate is placed in $SiO_2$ framework, and this can be easily confirmed by a peak of 210 to 230 mm in ultraviolet-visible absorption spectra. In addition, Ti of $TiO_2$ is usually 6-coordination, whereas Ti of titanosilicate is 4-coordination. This can be easily confirmed by measuring coordination number in a Ti-K-edge XAFS analysis.

Examples of the titanosilicate used in the present invention includes crystalline titanosilicates such as, in terms of the framework type code by IZA (International Zeolite Association), TS-2 having MEL structure, Ti-ZSM-12 having MTW structure (e.g., one described in Zeolites 15, 236-242, (1995)), Ti-Beta having BEA structure (e.g., one described in Journal of Catalysis 199, 41-47, (2001)), Ti-MWW having MWW structure (e.g., one described in Chemistry Letters 774-775, (2000)), Ti-UTD-1 having DON structure (e.g., Zeolites 15, 519-525, (1995)), etc.

Examples of the lamellar titanosilicate include a titanosilicate having a structure with expanded interlayers in MWW structure such as Ti-MWW precursor (e.g., one described in JP 2003-327425 A), Ti-YNU-1 (e.g. one described in Angewande Chemie International Edition 43, 236-240, (2004)), etc.

Mesoporous titanosilicate is a generic name of titanosilicates usually having periodic pore structures of diameters ranging from 2 to 10 nm and examples thereof include Ti-MCM-41 (e.g., one described in Microporous Materials 10, 259-271, (1997)), Ti-MCM-48 (e.g., one described in Chemical Communications 145-146, (1996)), Ti-SBA-15 (e.g., one described in Chemistry of Materials 14, 1657-1664, (2002)), etc. Further examples of the titanosilicate include a titanosilicate having features of both mesoporous titanosilicate and titanosilicate zeolite, such as Ti-MMM-1 (e.g. one described in Microporous and Mesoporous Materials 52, 11-18, (2002)).

Among the titanosilicates used in the present invention, a crystalline titanosilicate or a lamellar titanosilicate which has pores of 12 or more membered oxygen rings is preferred. As the crystalline titanosilicate having pores of 12 or more membered oxygen rings, Ti-ZSM-12, Ti-Beta, Ti-MWW and Ti-UTD-1 are mentioned.

As the lamellar titanosilicate having pores of 12 or more membered oxygen rings, Ti-MWW precursor and Ti-YNU-1 are mentioned. As a more preferred titanosilicate, Ti-MWW and Ti-MWW precursor are mentioned.

Usually, the titanosilicate used in the present invention can be synthesized by such a method that a surfactant is used as a template or a structure directing agent, a titanium compound and a silicon compound are hydrolyzed, if necessary, followed by improvement of crystallization or periodic regularity of pores by hydrothermal synthesis etc., and then the surfactant is removed by calcining or extraction.

Usually, the crystalline titanosilicate having MWW structure is prepared as follows. Namely, a silicon compound and a titanium compound are hydrolyzed in the presence of a structure directing agent to prepare a gel. Then, the resultant gel is subjected to heat treatment in the presence of water such as hydrothermal synthesis, etc. to prepare a lamellar precursor of crystal. Then, the resultant lamellar precursor of crystal is subjected to crystallization by calcination to prepare the crystalline titanosilicate having MWW structure.

The titanosilicate used in the present invention includes that silylized with a silylizing agent such as 1,1,1,3,3,3-hexamethyldisilazan, etc. Since silylization further enhances activity or selectivity, a silylized titanosilicate is also a preferred titanosilicate (for example, silylized Ti-MWW, etc.).

In addition, the titanosilicate can be used after it is activated by treatment with a hydrogen peroxide solution at an appropriate concentration. Usually, the concentration of the hydrogen peroxide solution can be in a range of 0.0001% to 50% by weight. The solvent of hydrogen peroxide solution is not particularly limited, but water or a solvent used for a propylene oxide synthesis reaction is convenient and preferable from the industrial view point.

As the quinoid compound, there are two types, i.e., a p-quinoid compound and a o-quinoid compound, both are included in the quinoid compound used in the present invention.

Examples of the quinoid compound include a phenanthraquinone compound and a p-quinoid compound represented by the formula (1):

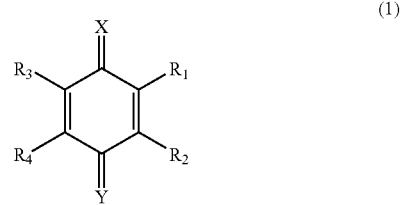

wherein $R_1$, $R_2$, $R_3$ and $R_4$ represent a hydrogen atom or, each adjacent $R_1$ and $R_2$, or $R_3$ and $R_4$ are independently bonded to each other at their terminal ends, and form a benzene ring optionally substituted with an alkyl group or a hydroxyl group, or a naphthalene ring optionally substituted with an alkyl group or a hydroxyl group together with the carbon atoms of the quinone to which they are bonded, and X and Y are the same or different and represent an oxygen atom or a NH group.

Examples of the compound represented by the formula (1) include (1) a quinone compound (1A): the compound represented by the formula (1), wherein $R_1$, $R_2$, $R_3$ and $R_4$ are a hydrogen atom, and both X and Y are an oxygen atom;

(2) a quinone-imine compound (1B): the compound represented by the formula (1), wherein $R_1$, $R_2$, $R_3$ and $R_4$ are a hydrogen atom, X is an oxygen atom, and Y is a NH group; and (3) a quinone-diimine compound (1C): the compound represented by the formula (1), wherein $R_1$, $R_2$, $R_3$ and $R_4$ are a hydrogen atom, and both X and Y are a NH group.

The quinoid compound of the formula (1) includes a anthraquinone compound represented by the formula (2):

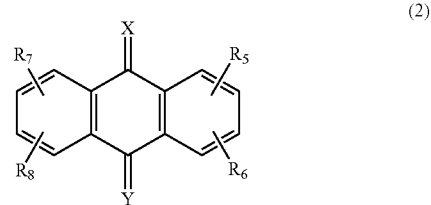

wherein X and Y are as defined in the formula (1), $R_5$, $R_6$, $R_7$ and $R_8$ are the same or different, and represent a hydrogen atom, a hydroxyl group, or an alkyl group (e.g., $C_1$-$C_5$ alkyl such as methyl, ethyl, propyl, butyl, pentyl, etc.).

In the formula (1) and formula (2), preferably, X and Y represent an oxygen atom. The quinoid compound represented by the formula (1) wherein X and Y are an oxygen atom is particularly referred to as quinone compound or p-quinone compound, and the quinoid compound represented by the formula (2) wherein X and Y are an oxygen atom is particularly referred to as anthraquinone compound.

Examples of the dihydro-form of the quinoid compound include dihydro-forms of the compounds represented by the foregoing formulas (1) and (2), i.e. compounds represented by the formulas (3) and (4):

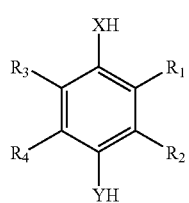

(3)

wherein $R_1$, $R_2$, $R_3$, $R_4$, X and Y are as defined in the foregoing formula (1); and

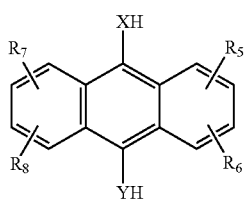

(4)

wherein X, Y, $R_5$, $R_6$, $R_7$ and $R_8$ are as defined in the foregoing formula (2).

In the formula (3) and formula (4), preferably, X and Y represent an oxygen atom. The dihydro-form of quinoid compound represented by the formula (3) wherein X and Y are an oxygen atom is particularly referred to as dihydroquinone compound or dihydro ρ-quinone compound, and the dihydro-form of quinoid compound represented by the formula (4) wherein X and Y are an oxygen atom is particularly referred to as dihydroanthraquinone compound.

Examples of the phenanthraquinone compound include 1,4-phenanthraquinone as a ρ-quinoid compound and 1,2-, 3,4-, and 9,10-phenanthraquinone as o-quinoid compounds.

Specific examples of the quinone compound include benzoquinone, naphthoquinone, anthraquinone, 2-alkylanthraquinone compounds such as 2-ethylanthraquinone, 2-t-bytylanthraquinone, 2-amylanthraquinone, 2-methylanthraquinone, 2-butylanthraquinone, 2-t-amylanthraquinone, 2-isopropylanthraquinone, 2-s-butylanthraquinone and 2-s-amylanthraquinone, 2-hydroxyanthraquinone, polyalkylanthraquinone compounds such as 1,3-diethylanthraquinone, 2,3-dimethylanthraquinone, 1,4-dimethylanthraquinone and 2,7-dimethylanthraquinone, poylhydroxyanthraquinone such as 2,6-dihydroxyanthraquinone, naphthoquinone and a mixture thereof.

Preferred examples of the quinoid compound include anthraquinone, and 2-alkylanthraquinone compounds (in formula (2), X and Y are an oxygen atom, $R_5$ is an alkyl group substituted at 2 position, $R_6$ represents a hydrogen atom, and $R_7$ and $R_8$ represent a hydrogen atom). Preferred examples of the dihydro-form of quinoid compound include the corresponding dihydro-forms of these preferred quinoid compounds.

The addition of the quinoid compound or the dihydro-form of quinoid compound (hereinafter, abbreviated as the quinoid compound derivative) to a reaction solvent can be carried out by first dissolving the quinoid compound derivative in a liquid phase and then subjecting it to the reaction. For example, a hydride compound of the quinoid compound such as hydroquinone or 9,10-anthracenediol may be added to a liquid phase, followed by oxidation with oxygen in a reactor to generate the quinoid compound and use it in the reaction.

Further, the quinoid compounds used in the present invention including the quinoid compounds exemplified above may become dihydro-forms of partly hydrogenated quinoid compounds depending on reaction conditions, and these compounds may also be used.

Hereinafter, the amount of the quinoid compound will be explained. In the present invention, the amount of the dihydro-form of quinoid compound can be the same as that of the quinoid compound.

Usually, the amount of the quinoid compound to be used can be in a range of 0.001 mmol/kg to 500 mmol/kg per unit weight of a solvent (unit weight of water, an organic solvent or a mixture thereof). A preferred amount of the quinoid compound is 0.01 mmol/kg to 50 mmol/kg.

Usually, the reaction of the present invention is carried out in a liquid phase of water, an organic solvent or a mixture thereof. To the liquid phase is added the quinoid compound, the dihydro-form of quinoid compound or a mixture thereof, and the quinoid compound derivative is preferably used by dissolving it in a liquid phase. Since the quinoid compound derivative tends to act more efficiently when a liquid phase contains an organic solvent, an epoxy compound can be obtained with a good selectivity even when an amount of the quinoid compound derivative used is reduced as compared with the case where the liquid phase contains no organic solvent. The organic solvent of the present invention means an organic compound which alone is in liquid at a reaction temperature and reaction pressure. Examples of the organic solvent include alcohols, ketones, nitrites, ethers, aliphatic hydrocarbons, aromatic hydrocarbons, halogenated hydrocarbons, esters, glycols, or a mixture thereof. Examples of the suitable solvent which can suppress sequentially production of by-products due to reaction with water or alcohol in a synthesis reaction of an epoxy compound include linear or branched saturated aliphatic nitrites and aromatic nitrites. Examples of these nitrile compounds include $C_2$-$C_4$ alkyl nitrile such as acetonitrile, propionitrile, isobutyronitrile and butyronitrile, and benzonitrile, with acetonitrile being preferred.

In case where a mixture of water and an organic solvent is used, usually, the ratio of water and the organic solvent is 90:10 to 0.01:99.99 by weight, preferably 50:50 to 0.01:99.99. When the ratio of water is too large, sometimes, an epoxy compound is apt to react with water, which causes deterioration due to ring opening, resulting in lowering the selectivity of the epoxy compound. To the contrary, when the ratio of an organic solvent is too large, recovery costs of the solvent becomes high.

In the process of the present invention, it is also effective to add a salt selected from an ammonium salt, an alkyl ammonium salt or an alkyl aryl ammonium salt to a reaction solvent together with the titanosilicate, the noble metal catalyst and the quinoid compound, because such a salt can prevent the lowering of catalyst activity or can further increase catalyst activity to enhance utilization efficiency of hydrogen. Usually, the amount of a salt selected from an ammonium salt, an alkyl ammonium salt or an alkyl aryl ammonium salt to be added is 0.001 mmol/kg to 100 mmol/kg per unit weight of solvent (in the case of a mixture of water and an organic solvent, the total weight thereof).

Examples of the salt selected from an ammonium salt, an alkyl ammonium salt or an alkyl aryl ammonium salt include a salt composed of:
(1) an anion selected from, sulfate ion, hydrogen sulfate ion, carbonate ion, hydrogen carbonate ion, phosphate ion, hydrogen phosphate ion, dihydrogen phosphate ion, hydrogen pyrophosphate ion, pyrophosphate ion, halogen ion, nitrate ion, hydroxide ion or $C_1$-$C_{10}$ carboxylate ion; and (2) a cation selected from ammonium, alkyl ammonium or alkyl aryl ammonium.

Examples of the $C_1$-$C_{10}$ carboxylate ion include formate ion, acetate ion, propionate ion, butyrate ion, valerate ion, caproate ion, caprylate ion and caprinate ion.

Examples of the alkyl ammonium include tetramethylammonium, tetraethylammonium, tetra-n-propylammonium, tetra-n-butylammonium and cetyltrimethylammonium.

Preferred examples of the salt selected from an ammonium salt, an alkyl ammonium salt or an alkyl aryl ammonium salt include ammonium salts of inorganic acids such as ammonium sulfate, ammonium hydrogen sulfate, ammonium carbonate, ammonium hydrogen carbonate, diammonium hydrogen phosphate, ammonium dihydrogen phosphate, ammonium phosphate, ammonium hydrogen pyrophosphate, ammonium pyrophosphate, ammonium chloride and ammonium nitrate; or ammonium salts of $C_1$ to $C_{10}$ carboxylic acids such as ammonium acetate, and a preferred ammonium salt is ammonium dihydrogen phosphate.

The olefin used in the present invention means a hydrocarbon having one or more carbon-carbon double bonds. Examples of the olefin used in the present invention include aliphatic olefins such as ethylene, propylene, 1-butene, 2-butene, 1-pentene, 1-hexene and 2-hexene; cyclic olefins such as cyclopentene and cyclohexene; diolefins such as butadiene; and an olefin having an aromatic ring such as styrene, etc.

The process of the present invention can be preferably used in the production of epoxy compounds such as ethylene oxide, propylene oxide, 1-butene oxide, 2-butene oxide, 1-pentene oxide, 1-hexene oxide and 2-hexene oxide from corresponding $C_2$-$C_6$ olefins such as ethylene, propylene, 1-butene, 2-butene, 1-pentene, 1-hexene, 2-hexene, cyclopentene, cyclohexene and butadiene Examples of the reaction of the process of the present invention include, for example, a fixed bed reaction, an agitating tank type reaction, a fluidized bed reaction, a moving bed reaction, a bubble column type reaction, tubular type reaction, a circulating reaction, and the like.

Usually, the partial pressure ratio of oxygen and hydrogen fed to a reactor is in a range of 1:50 to 50:1. A preferable partial pressure ratio of oxygen and hydrogen is 1:2 to 10:1. When the partial pressure ratio of oxygen and hydrogen (oxygen/hydrogen) is too high, sometimes, the production rate of an epoxy compound is lowered. On the other hand, when the partial pressure ratio of oxygen and hydrogen (oxygen/hydrogen) is too low, sometimes, selectivity of an epoxy compound is lowered due to the increase in paraffin by-products. Oxygen and hydrogen gases used in the present reaction can be used by diluting them with a gas for dilution. Examples of the gas for dilution include nitrogen, argon, carbon dioxide, methane, ethane and propane. Although the concentration of the gas for dilution is not particularly limited, the reaction is carried out by diluting oxygen or hydrogen, where necessary.

Examples of the oxygen source include oxygen gas or air. As the oxygen gas, there can be used a cheap oxygen gas produced by a pressure swing method, a high purity oxygen gas produced by cryogenic separation, or the like.

Usually, the reaction temperature of the present invention is 0° C. to 150° C., preferably 40° C. to 90° C. When the reaction temperature is too low, the reaction rate becomes slow. On the other hand, when the reaction temperature is too high, by-products increase due to side reactions.

The reaction pressure is not particularly limited, and generally 0.1 MPa to 20 MPa in gauge pressure, preferably 1 MPa to 10 MPa. When the reaction pressure is too low, dissolution of raw material gases becomes insufficient, and the reaction rate becomes slow. When the reaction pressure is too high, costs of reaction facilities increase. Recovery of the product of the present invention, i.e., the resulting epoxy compound can be carried out by conventional distillation separation. Unreacted olefin and/or solvent(s) can also be recovered, for example, by distillation separation, membrane filtration, or the like, if necessary.

The present invention will be explained with reference to Examples below, but the present invention is not limited thereto.

EXAMPLE 1

Ti-MWW used in this reaction was prepared by a method described in Chemistry Letters 774-775, (2000). Piperidine (9.1 kg), purified water (25.6 kg), boric acid (6.2 kg), TBOT (tetra-n-butylorthotitanate; 0.54 kg) and fumed silica (cab-o-sil M7D; 4.5 kg) were placed in an autoclave and stirred at room temperature under an argon atmosphere to prepare a gel. The gel was aged for 1.5 hours, and the autoclave was closed. After the temperature was raised over 10 hours with stirring, it was maintained at 170° C. for 168 hours to conduct hydrothermal synthesis, thereby obtaining a suspension. The resultant suspension was filtered, and then washed with water until the filtrate became about pH 10. Then, the filter cake was dried at 50° C. to obtain a white powder still in a wet state. To 350 g of the resultant powder was added 3.5 L of 13% by weight nitric acid was added, and the mixture was refluxed for 20 hours. Then, the mixture was filtered, washed with water until it became approximately neutral, and dried sufficiently at 50° C. to obtain 98 g of a white powder. This white powder was subjected to X-ray diffraction pattern measurement by using an X-ray diffraction apparatus using copper K-alpha radiation. As a result, Ti-MWW precursor was confirmed. The resultant Ti-MWW precursor was calcined at 530° C. for 6 hours to obtain a Ti-MWW catalyst powder. It was confirmed that the resultant powder had MWW structure by measuring X-ray diffraction pattern, and the content of titanium by ICP emission analysis was 0.9% by weight.

Catalyst A

As with the above, Pd/carbon black (CB) catalyst used in this reaction was prepared according to a method described in US 2005-0014636 A. In a 500 mL pear-shaped flask, 500 mL of an aqueous solution containing palladium chloride (0.56 mmol), platinum chloride (0.006 mmol), sodium polyacrylate (molecular weight: 1200, 1.27 mmol) and hydrogen chloride (30 mmol) was placed and stirred at room temperature for 1 hour in an atmosphere of air. To this mixture, hydrogen gas was introduced at 100 mL/min. at room temperature for 20 minutes to form a Pd colloid. To the above colloidal solution was added 6 g of commercially available CB (Seast 9, manufactured by Tokai Carbon Co., Ltd.) and the mixture was stirred for 8 hours. After completion of stirring, water was removed with a rotary evaporator, and the residue was further dried at 50° C. for 12 hours under vacuum. The resultant catalyst precursor powder was calcined at 300° C. for 6 hours under a nitrogen atmosphere to obtain Pd/CB catalyst. According to ICP emission analysis, the content of palladium was 1.01% by weight and the content of platinum was 0.02% by weight.

An autoclave of 0.5 L capacity was used as a reactor in the reaction. To the reactor were fed raw material gases of propylene/oxygen/hydrogen/nitrogen having a ratio of 4/8/1/87 (volume ratio) at a rate of 16 L/hour and a solution of water/acetonitrile=20/80 (weight ratio) containing anthraquinone of 0.7 mmol/kg at a rate of 108 mL/hour, while the reaction mixture was took out through a filter from the reactor, thereby conducting a continuous reaction under conditions of temperature at 60° C., pressure at 0.8 MPa (gauge pressure) and retention time of 90 minutes. During this time, 131 g of the reaction solvent (water/acetonitrile=20/80 (weight ratio)), 0.133 g of Ti-MWW and 0.03 g of Pd/CB of 0.03 g were present in the reaction mixture in the reactor. The liquid and gas phases took out after 5 hours from the initiation of the reaction were analyzed by gas chromatography. As a result, the activity of propylene oxide generation relative to the unit weight of Ti-MWW was 3.18 mmol-PO/g-Ti-MWW·h, selectivity based on propylene was 89% and selectivity based on hydrogen was 31%.

EXAMPLE 2

By using 100 g of a solution of water/acetonitrile=20/80 (weight ratio) containing 0.1% by weight of hydrogen peroxide, 0.6 g of Ti-MWW powder obtained in Example 1 was treated at room temperature for 1 hour and the mixture was washed with 500 mL of water and filtered. The resulting mixture was used in the same reaction as that of Example 1. Further, the same reaction as that of Example 1 was also carried out by using a solution of water/acetonitrile=20/80 containing 9,10-phenanthraquinone of 0.7 mmol/kg, instead of the solution of water/acetonitrile=20/80 containing anthraquinone of 0.7 mmol/kg. The liquid and gas phases took out after 5 hours from the initiation of the reaction were analyzed by gas chromatography. As a result, the activity of propylene oxide generation relative to the unit weight of Ti-MWW was 2.14 mmol-PO/g-Ti-MWW·h, selectivity based on propylene was 99% and selectivity based on hydrogen was 21%.

EXAMPLE 3

According to the same manner as that in Example 2, the reaction was carried out except that a solution of water/acetonitrile=20/80 containing benzoquinone of 0.7 mmol/kg was used in place of the solution of water/acetonitrile=20/80 containing 9,10-phenanthraquinone of 0.7 mmol/kg. The liquid and gas phases took out after 5 hours from the initiation of the reaction were analyzed by gas chromatography. As a result, the activity of propylene oxide generation relative to the unit weight of Ti-MWW was 3.30 mmol-PO/g-Ti-MWW·h, selectivity based on propylene was 84% and selectivity based on hydrogen was 23%.

EXAMPLE 4

According to the same manner as that of Example 2, the reaction was carried out except that a solution of water/acetonitrile=20/80 containing 2-ethylanthraquinone of 0.7 mmol/kg was used in place of the solution of water/acetonitrile=20/80 containing 9,10-phenanthraquinone of 0.7 mmol/kg. The liquid and gas phases took out after 5 hours from the initiation of the reaction were analyzed by gas chromatography. As a result, the activity of propylene oxide generation relative to the unit weight of Ti-MWW was 3.67 mmol-PO/g-Ti-MWW·h, selectivity based on propylene was 93% and selectivity based on hydrogen was 33%.

EXAMPLE 5

According to the same manner as that of Example 2, the reaction was carried out except that a solution of water/acetonitrile=20/80 containing 2,6-dihydroxyanthraquinone of 0.7 mmol/kg was used in place of the solution of water/acetonitrile=20/80 containing 9,10-phenanthraquinone of 0.7 mmol/kg. The liquid and gas phases took out after 5 hours from the initiation of the reaction were analyzed by gas chromatography. As a result, the activity of propylene oxide generation relative to the unit weight of Ti-MWW was 2.63 mmol-PO/g-Ti-MWW·h, selectivity based on propylene was 88% and selectivity based on hydrogen was 30%.

EXAMPLE 6

According to the same manner as that of Example 2, the reaction was carried out except that a solution of water/acetonitrile=20/80 containing hydroquinone of 0.7 mmol/kg was used in place of the solution of water/acetonitrile=20/80 containing 9,10-phenanthraquinone of 0.7 mmol/kg. The liquid and gas phases took out after 5 hours from the initiation of the reaction were analyzed by gas chromatography. As a result, the activity of propylene oxide generation relative to the unit weight of Ti-MWW was 3.26 mmol-PO/g-Ti-MWW·h, selectivity based on propylene was 83% and selectivity based on hydrogen was 23%.

EXAMPLE 7

According to the same manner as that of Example 2, the reaction was carried out except that a solution of water/acetonitrile=20/80 containing anthraquinone of 0.7 mmol/kg and ammonium dihydrogen phosphate of 0.7 mmol/kg was used in place of the solution of water/acetonitrile=20/80 containing 9,10-phenanthraquinone of 0.7 mmol/kg. The liquid and gas phases took out after 5 hours from the initiation of the reaction were analyzed by gas chromatography. As a result, the activity of propylene oxide generation relative to the unit weight of Ti-MWW was 3.53 mmol-PO/g-Ti-MWW·h, selectivity based on propylene was 90% and selectivity based on hydrogen was 45%.

EXAMPLE 8

According to the same manner as that of Example 1, the reaction was carried out except that the raw material gases of propylene/oxygen/hydrogen/nitrogen having a ratio of 4/8/3/85 (volume ratio) was used in place of the raw material gases of propylene/oxygen/hydrogen/nitrogen having a ratio of 4/8/1/87 (volume ratio), and Ti-MWW precursor was used in place of Ti-MWW. The liquid and gas phases took after 5 hours from the initiation of the reaction were analyzed by gas chromatography. As a result, the activity of propylene oxide generation relative to the unit weight of Ti-MWW precursor was 10.19 mmol-PO/g-Ti-MWW precursor·h, selectivity based on propylene was 96% and selectivity based on hydrogen was 19%.

Comparative Example 1

According to the same manner as that in Example 1, the reaction was carried out except that a solution of water/acetonitrile=20/80 containing no anthraquinone was used in place of the solution of water/acetonitrile=20/80 containing anthraquinone of 0.7 mmol/kg. The liquid and gas phases took out after 5 hours from the initiation of the reaction were analyzed by gas chromatography, As a result, the activity of propylene oxide generation relative to the unit weight of Ti-MWW was 1.02 mmol-PO/g-Ti-MWW·h, selectivity based on propylene was 50% and selectivity based on hydrogen was 11%.

Comparative Example 2

According to the same manner as that of Example 8, the reaction was carried out except that an aqueous solution of water/acetonitrile=20/80 was used in place of the solution of water/acetonitrile=20/80 containing anthraquinone of 0.7 mmol/kg. The liquid and gas phases took out after 5 hours from the initiation of the reaction were analyzed by gas chromatography. As a result, the activity of propylene oxide generation relative to the unit weight of Ti-MWW precursor was 7.33 mmol-PO/g-Ti-MWW precursor·h, selectivity based on propylene was 66% and selectivity based on hydrogen was 13%.

Comparative Example 3

According to the same manner as that of Example 1, the reaction was carried out except that an aqueous solution containing hydroquinone of 545 mmol/kg was used in place of the solution of water/acetonitrile=20/80 containing anthraquinone of 0.7 mmol/kg, and TS-1 containing titanium of 1.3% by weight was used in place of Ti-MWW. The liquid and gas phases took out after 5 hours from the initiation of the reaction were analyzed by gas chromatography. As a result, the activity of propylene oxide generation relative to the unit weight of TS-1 was 0.28 mmol-PO/g-TS-1·h, selectivity based on propylene was 37% and selectivity based on hydrogen was 8%.

INDUSTRIAL APPLICABILITY

According to the present invention, an epoxy compound can be efficiently produced from an olefin, oxygen and hydrogen using a quinoid compound, etc.

The invention claimed is:

1. A process for producing an epoxy compound which comprises simultaneously reacting an olefin, oxygen and hydrogen in a liquid phase in the presence of a titanosilicate selected from the group consisting of a crystalline titanosilicate having MEL structure, MTW structure, BEA structure, MWW structure or DON structure, a mesoporous titanosilicate and a lamellar titanosilicate, a noble metal catalyst, and a quinoid compound or a dihydro-form of quinoid compound.

2. The process according to claim 1, wherein the titanosilicate is a crystalline titanosilicate having MWW structure, or a lamellar titanosilicate.

3. The process according to claim 1, wherein the titanosilicate is a crystalline titanosilicate having MWW structure, or a precursor of Ti-MWW.

4. The process according to claim 1, wherein the noble metal catalyst is palladium, platinum, ruthenium, rhodium, iridium, osmium, gold, or an alloy or a mixture thereof.

5. The process according to claim 4, wherein the noble metal catalyst is palladium.

6. The process according to claim 1, wherein the olefin is a $C_2$-$C_6$ olefin.

7. The process according to claim 6, wherein the olefin is propylene.

8. The process according to claim 1, wherein the quinoid compound is a phenanthraquinone compound or a compound represented by the formula (1):

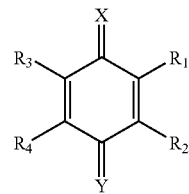

(1)

wherein $R_1$, $R_2$, $R_3$ and $R_4$ represent a hydrogen atom or, each adjacent $R_1$ and $R_2$, or $R_3$ and $R_4$ are independently bonded to each other at their terminal ends, and form a benzene ring optionally substituted with an alkyl group or a hydroxyl group, or a naphthalene ring optionally substituted with an alkyl group or a hydroxyl group together with the carbon atoms of the formula (1) to which they are bonded, and X and Y are the same or different and represent an oxygen atom or a NH group.

9. The process according to claim 1, wherein the quinoid compound is a phenanthraquinone compound or a compound represented by the formula (2):

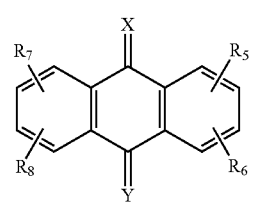

(2)

wherein X and Y are the same or different, and represent an oxygen atom or a NH group, and $R_5$, $R_6$, $R_7$ and $R_8$ are the same or different, and represent a hydrogen atom, a hydroxyl group or an alkyl group.

10. The process according to claim 8 or 9, wherein the X and Y are both an oxygen atom.

11. The process according to claim 1, wherein the liquid phase is that containing an organic solvent.

12. The process according to claim 11, wherein the organic solvent is acetonitrile.

13. The process according to claim 11, wherein the liquid phase is a mixture of organic solvent and water, and the ratio of organic solvent and water is 90:10 to 0.01:99.99.

14. The process according to claim 11, wherein the liquid phase contains a salt selected from the group consisting of an ammonium salt, an alkyl ammonium salt, and an alkyl aryl ammonium salt.

15. The process according to claim 14, wherein the salt is a salt composed of (1) an anion selected from the group consisting of sulfate ion, hydrogen sulfate ion, carbonate ion, hydrogen carbonate ion, phosphate ion, hydrogen phosphate ion, dihydrogen phosphate ion, hydrogen pyrophosphate ion, pyrophosphate ion, halogen ion, nitrate ion, hydroxide ion, and C1-C10 carboxylate ion; and (2) a cation selected from the group consisting of ammonium, alkyl ammonium and alkyl aryl ammonium.

16. The process according to claim 14, wherein the salt is an ammonium salt.

17. The process according to claim 14, wherein the salt selected from an is ammonium dihydrogen phosphate.

* * * * *